United States Patent
Williamson

(10) Patent No.: US 10,495,618 B2
(45) Date of Patent: Dec. 3, 2019

(54) MULTI-CHANNEL DETECTOR

(71) Applicant: Xtralis Global, Dublin (IE)

(72) Inventor: Alasdair James Williamson, Worthing (GB)

(73) Assignee: Xtralis Global, Dublin (IE)

(*) Notice: Subject to any disclaimer, the term of this patent is extended or adjusted under 35 U.S.C. 154(b) by 155 days.

(21) Appl. No.: 15/122,778

(22) PCT Filed: Feb. 27, 2015

(86) PCT No.: PCT/EP2015/054203
§ 371 (c)(1),
(2) Date: Aug. 31, 2016

(87) PCT Pub. No.: WO2015/132161
PCT Pub. Date: Sep. 11, 2015

(65) Prior Publication Data
US 2017/0082586 A1 Mar. 23, 2017

Related U.S. Application Data

(60) Provisional application No. 61/949,187, filed on Mar. 6, 2014.

(51) Int. Cl.
*G01N 33/00* (2006.01)
*G01N 15/10* (2006.01)

(52) U.S. Cl.
CPC ......... *G01N 33/0022* (2013.01); *G01N 15/10* (2013.01); *G01N 33/0031* (2013.01)

(58) Field of Classification Search
CPC . G01N 33/0022; G01N 15/10; G01N 33/0031
See application file for complete search history.

(56) References Cited

U.S. PATENT DOCUMENTS

| 3,849,653 A | 11/1974 | Sakaide et al. |
| 4,361,810 A | 11/1982 | Schlosser |
| 4,670,405 A * | 6/1987 | Stetter ................ G01N 33/0031 422/98 |
| 4,818,348 A | 4/1989 | Stetter |

(Continued)

FOREIGN PATENT DOCUMENTS

| CN | 101727727 | 6/2010 |
| CN | 104299353 | 1/2015 |

(Continued)

OTHER PUBLICATIONS

"International Application No. PCT/EP2015/054203, International Search Report and Written Opinion dated May 22, 2015", (May 22, 2015), 9 pgs.

(Continued)

*Primary Examiner* — Xin Y Zhong
(74) *Attorney, Agent, or Firm* — Brooks, Cameron & Huebsch, PLLC

(57) ABSTRACT

A multi-channel particle and/or gas detector including an array of detector elements held in a housing structure, the structure configured to provide each detector element with an inlet and an outlet, wherein each inlet, detector element and outlet form a dedicated detector channel which operatively communicates with a sampling tube.

14 Claims, 4 Drawing Sheets

(56) References Cited

U.S. PATENT DOCUMENTS

| | | | |
|---|---|---|---|
| 5,106,756 A * | 4/1992 | Zaromb | G01N 27/4045 |
| | | | 422/70 |
| 2002/0014106 A1* | 2/2002 | Srinivasan | B01J 19/0046 |
| | | | 73/23.42 |
| 2010/0319465 A1 | 12/2010 | Ajay et al. | |
| 2013/0145824 A1 | 6/2013 | Lee et al. | |

FOREIGN PATENT DOCUMENTS

| | | |
|---|---|---|
| JP | H-5142109 A | 6/1993 |
| JP | H102870 A | 1/1998 |
| JP | 2010276515 A | 12/2010 |
| WO | WO-2015132161 | 9/2015 |

OTHER PUBLICATIONS

Becker, T. H., et al., "Air pollution monitoring using tin-oxide-based microreactor systems", Sensors and Actuators B: Chemical, vol. 69, Issues 1-2, Sep. 10, 2000, pp. 108-119, (Sep. 10, 2000), 108-119.
"Chinese Application No. 201580005797.7, Notification of the First Office Action dated Jan. 6, 2017", (Jan. 6, 2017), 18 pgs.
"Japanese Application No. 2016-543232, Notification of Reasons for Refusal dated Sep. 26, 2018", (Sep. 26, 2018), 9 pgs.

* cited by examiner

MULTI-CHANNEL DETECTOR

PRIORITY CLAIM TO RELATED APPLICATIONS

This application is a U.S. national stage application filed under 35 U.S.C. § 371 from International Application Ser. No. PCT/EP2015/054203, which was filed 27 Feb. 2015, and published as WO2015/132161 on 11 Sep. 2015, and which claims priority to U.S. Provisional Application No. 61/949,187, filed 6 Mar. 2014, which applications and publication are incorporated by reference as if reproduced herein and made a part hereof in their entirety, and the benefit of priority of each of which is claimed herein.

FIELD OF THE DISCLOSURE

The present disclosure generally relates to a multi-channel detector, and in particular to a multi-channel particle and/or gas detector, typically of the aspirated kind.

BACKGROUND

Multi-channel air-sampling systems with alarm capability are known. One example of such a system employs a rotary valve type detector that draws a combined air sample from a network of microbore flexible tubing from various sectors in a protected area. The detector then filters and analyses the sample in a laser detection chamber. When smoke particles are detected in the combined sample, the system is switched to sequentially scan the different sectors via the rotary valve to identify the sector, or sectors, with the smoke condition. It follows that, although this arrangement provides for multiple entry points into a detector, the detector needs to work sequentially through the various sector samples in order to identify the sector from which the problematic sample has originated. This process of detection has short-comings in that multiple samples can only be processed in series, while the detection process takes longer, limiting the number of channels that could be included within a single detector.

The present invention aims to provide an alternative multi-channel particle detector, which addresses some of the short-comings associated with the serial processing nature of the known systems.

Reference to any related art in the specification is not an acknowledgment or suggestion that this art forms part of the common general knowledge in any jurisdiction or that this art could reasonably be expected to be understood, regarded as relevant, and/or combined with other pieces of prior art by a skilled person in the art.

SUMMARY

According to a first aspect there is provided a multi-channel particle and/or gas detector including an array of detector elements held in a housing structure, the structure configured to provide each detector element with an inlet and an outlet, wherein each inlet, detector element and outlet form a dedicated detector channel which operatively communicates with a sampling tube.

The array of detector elements may be sensors of the same type thereby for each detector element to detect the same particle, gas, combination of particles or combination of gases.

Alternatively the array of detector elements may include different types of sensors, each type of sensor being configured to detect a different particle, gas, combination of particles or combination of gases.

Typically, the detector may include multiple arrays of detector elements, outlets of one array of detector elements being in fluid communication with inlets of an adjacent array of detector elements, thereby connecting multiple detector elements from different arrays in series within single detector channels. These multiple arrays may be stacked in-line within a single housing.

It will be appreciated that the modular construction of the detector facilitates stacking of a plurality of sub-assemblies, the number of sub-assemblies depending on the number of in-line detectors required. Each sub-assembly may include a preferably planar array of detector elements on opposite sides of which are mounted manifolds, preferably via sealing gaskets, the manifolds in turn being arranged to receive pneumatic fittings. The inlets or outlets of the pneumatic fittings may be configured to receive sampling tubes. For a stacking embodiment the pneumatic fittings on one or both sides of the array of detector elements (depending on how many sub-assemblies are in the stack) may have both ends configured to locate within manifolds so that a further manifold/detector array/manifold sub-assembly may be stacked on the existing sub-assembly. The stacked sub-assemblies are in turn enclosed in a casing.

Typically the multiple detector elements connected in series within a single detector channel are respectively configured to detect different particles, gases, combination of particles or combination of gases, thereby to provide multi-criteria detection of particles and/or gases within the particular detection channel of the detector.

The detector may include a plenum connected on one end thereof to the outlets of the detector elements, which plenum is in fluid communication with an aspirator in use causing air to flow through the array of detector elements. Preferably the aspirator is a fan or a pump.

Typically each of the sensors includes a detecting substrate configured to detect a particular particle or gas, wherein the detecting substrate is selected from one or more of the following: a printed circuit board, a ceramic, a composite device, a semiconductor, a micro-electro-mechanical system (MEMS) or the like.

The detecting substrate may be communicatively coupled to the inlet and outlet of each detector channel.

Each array of detector elements may be a planar array.

The detector may include a flow monitoring device associated with each or some of the detector channels.

As used herein, except where the context requires otherwise, the term "comprise" and variations of the term, such as "comprising", "comprises" and "comprised", are not intended to exclude further additives, components, integers or steps.

Further aspects of the present invention and further embodiments of the aspects described in the preceding paragraphs will become apparent from the following description, given by way of example and with reference to the accompanying drawings.

DETAILED DESCRIPTION OF THE EMBODIMENTS

A multi-channel particle and/or gas detector will now be described, by way of example only, with reference to the accompanying drawings.

Figure 1:
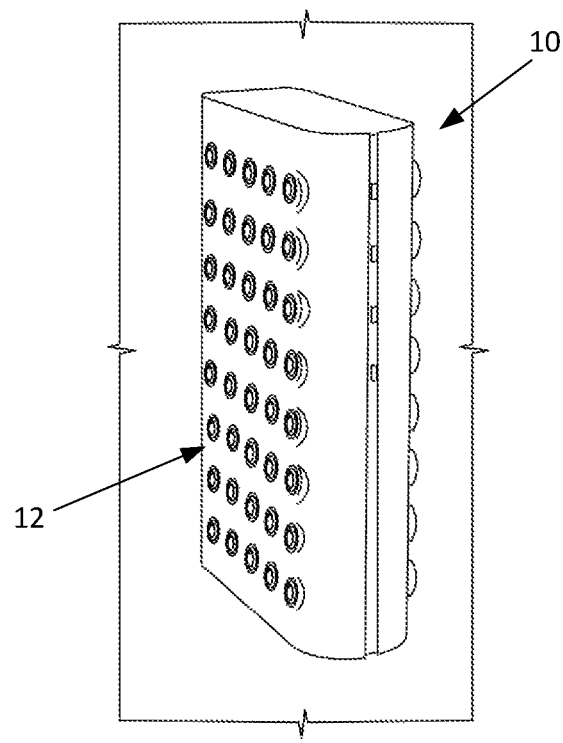
FIG. 1 shows a perspective view of a multi-channel particle and/or gas detector in accordance with an example embodiment.
Figure 2:
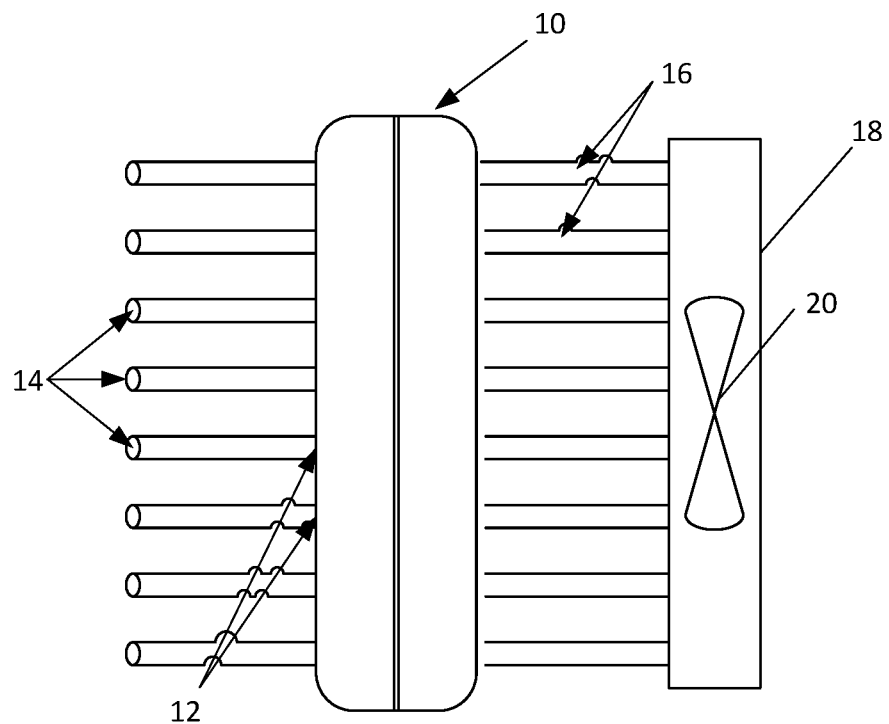
FIG. 2 is a schematic side view of the multi-channel particle and/or gas detector of FIG. 1 where the detector is connected to various sampling tubes and a plenum.

Turning first to FIGS. 1 and 2, a multi-channel particle and/or gas detector is generally indicated by reference numeral 10. The detector 10 comprises an array of detector elements, each of which forms part of a detector channel 12. The multiple detector channels 12, formed by the array of detector elements, may, in use, be connected to sampling tubes 14. These multiple sampling tubes 14 form part of a sampling network, with each sampling tube 14 having a number of air sample inlets in the form of sampling holes or sampling points located along the length of the tube. The sampling points are conveniently located in areas of interest thereby to allow detection of gas and/or particles in those areas.

The outlets of the multiple detector channels 12 are in turn connected to an aspirator configuration. In this example, the aspirator configuration is a plenum 18 which receives outputs from the detector 10. The plenum 18 is in fluid communication with an aspirator 20 which causes air to flow through the sampling tubes 14 and through the multiple detector channels 12. The aspirator 20 may be in the form of a fan or pump, or any other suitable device. As air is fed through the respective tubes 14 and associated channels 12, the detector elements perform gas and/or particle sampling in order to enable a monitoring system to raise appropriate alarms when minimum levels of particular particles or gases are detected.

The detector elements are used to detect the presence, and measure the concentration of gases or other volatile compounds from the various locations sampled. Among other uses, the detector 10 may be employed in a monitoring system to, for instance, detect the presence of a toxic gas, a flammable gas leak (in an effort to prevent fire), or flammable gas build-up (e.g., methane in sewage systems) and/or a gas or other volatile compound or smoke that is indicative of an impending fire (i.e. smouldering or melting materials) or pre-existing fire (i.e. burning materials) or the nature of a fire (e.g., the type of material that is burning).

In terms of the detection of a toxic gas, detector elements may for example be configured to detect ammonia released in an enclosed space, methyl isocyanate gas accidentally released from an industrial manufacturing plant, or carbon dioxide and/or carbon monoxide produced from a controlled fire event such as fuel fired furnaces, gas hot water heaters, gas stoves, gas dryers, space heaters, charcoal grills, fireplaces, vehicles (including build-up in car-parks), and lawn mowers.

Figure 3:
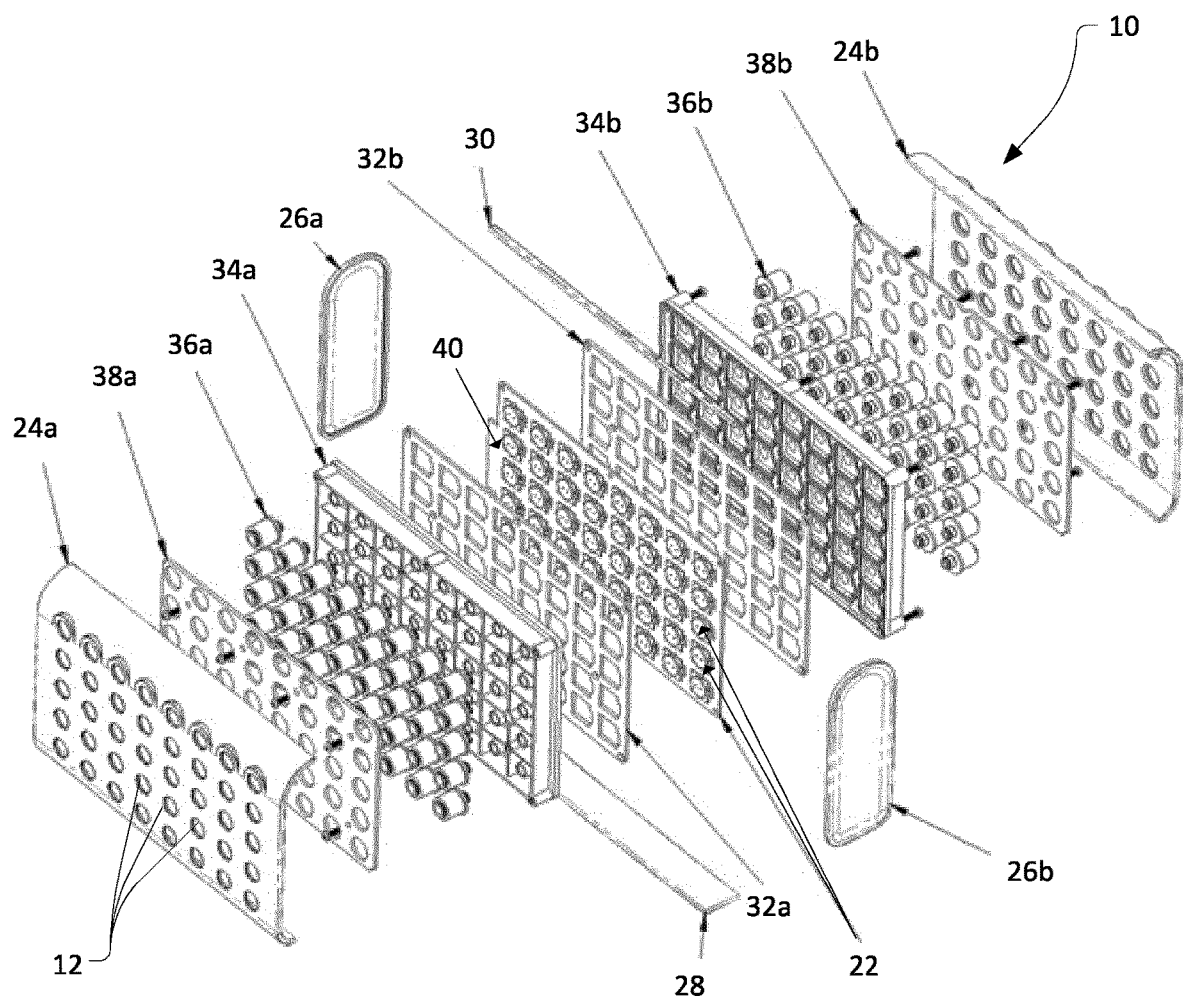
FIG. 3 is an exploded view of the multi-channel particle and/or gas detector of FIG. 1 showing a single planar array of detector elements and other components of the detector.

The multi-channel particle and/or gas detector 10 is now described in more detail with reference to FIGS. 3 and 4. FIG. 3 shows that the detector 10 comprises a forty channel (5×8) array of detector elements, shown as a planar array of sensors 22. It will be appreciated that the array need not be in a planar configuration. Each sensor 22 of the array of sensors includes a detecting substrate configured to detect a particular particle or gas type. In one example the sensor detects carbon monoxide using the electrochemical oxidation of CO, and has a measuring range of 1-1000 ppm CO, a response time of less than 30 seconds and a resolution of less than 1 ppm. The detecting substrate in the example is a PCB, but may also typically be selected from a ceramic, a composite device, a semiconductor, a micro-electro-mechanical system (MEMS) or the like.

The multi-channel detector 10 consists of a housing structure formed by side panels 24a and 24b, end covers 26a and 26b, a back sealing strip 28 and a front sealing strip 30. Within this housing, on each side of and, starting from the PCB-mounted array of sensors 22, are placed a sealing gasket 32a, 32b, a manifold 34a, 34b, an array of pneumatic push fittings 36a, 36b and an apertured fixing plate 38a, 38b. A common printed circuit board (PCB) 40 carries all the sensors 22 as specified above, with the PCB 40 being sandwiched between a respective pair of sealing gaskets and manifolds 32a and 34a, 32b and 34b. On each side of the PCB 40, the respective manifold and sealing gasket 32a and 34a, 32b and 34b are secured to the PCB 40 through screw fasteners. The arrays of pneumatic fittings 36a and 36b are in turn held in place by aperture fixing plates 38a and 38b also secured with screw fasteners to each of the manifolds 34a and 34b.

Figure 4:
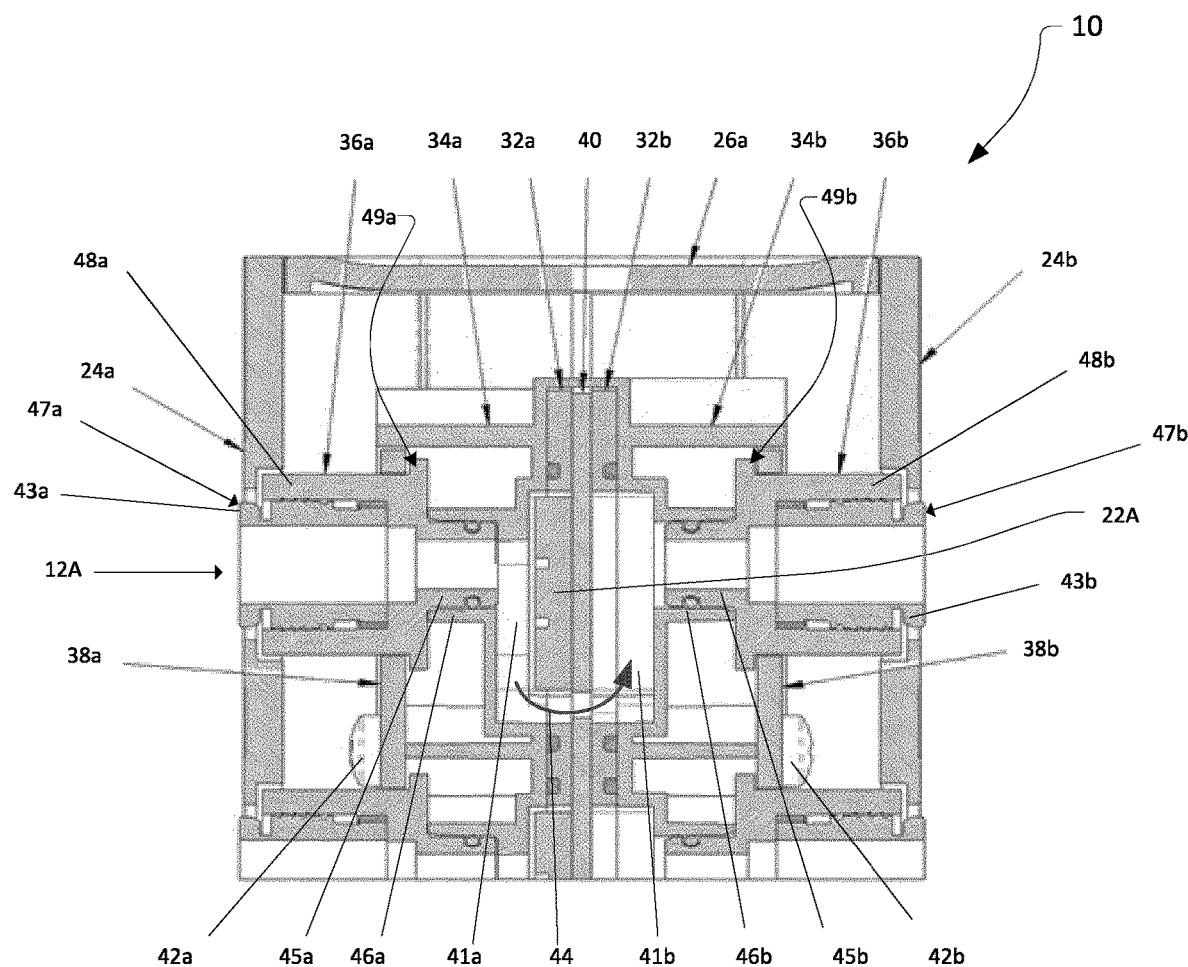
FIG. 4 is a cross-section of part of the multi-channel particle and/or gas detector of FIG. 1, showing the configuration of a single detector channel.

FIG. 4 shows clearly how the various above components fit snugly together. Each manifold 34a, 34b provides a sub-housing 41a, 41b which together accommodate a sensor 22A. A single detector channel 12A is shown by FIG. 4 to include an inlet defined by the pneumatic fitting 36a. Each pneumatic fitting 36a, 36b includes a resilient push fitting 43a, 43b for receiving a sampling tube. The pneumatic fitting 36a, 36b also includes an innermost spigot 45a, 45b which is received snugly within a complemental opening 46a, 46b in the manifold 34a, 34b. The fixing plates 38a and 38b are mounted to the respective manifolds 34a and 34b via screw fasteners 42a and 42b, with the apertures 47a, 47b in the fixing plates 38a and 38b passing over the outer tubular portions 48a, 48b of the pneumatic fittings 36a, 36b and abutting against intermediate flanges 49a, 49b of the fittings 36a, 36b to hold them in position. The detector channel 12A defines a flow path 44 through an opening in the PCB 40 adjacent the sensor 22A, the sub-housing 41 b of the manifold 34b and an outlet defined by the pneumatic fitting 36b. Air flows along the flow path 44 between the inlet and outlet of the detector channel 12A past the sensor 22A. The gaskets 32a and 32b provide an effective seal for isolating and confining the air flow along the flow path 44, and allowing the detecting substrate to be uniquely coupled to the inlet and outlet of each detector element in order for dedicated gas or particle detection to take place in respect of each detector channel in the array.

The common PCB 40 is used to communicate any detection of a gas or particles to the monitoring station, in one example embodiment by using a communication standard such as RS485 MODBUS.

The array of sensors 22 of the multi-channel detector 10 may, in one example embodiment, be the same type of sensor which would allow each sensor to detect the same particle, gas, combination of particles or combination of gases. For example, all the sensors may be fire sensors/ smoke detectors configured to detect the burning of a material. In such a configuration, various areas of interest may be connected to the detector 10 via sampling tubes 14, with all areas being monitored for fire.

Alternatively, the array of sensors 22 may be configured into multiple groups of different types of sensors, where each group of sensors detect the presence of a different particle, gas, combination of particles or combination of gases. For example, each row of sensors may be a different type of sensors, with one detector 10 therefore being able to detect various particles, gases or combinations from the same or different areas. This allows more design flexibility and ultimately measurement flexibility within a single detector.

Figure 5:
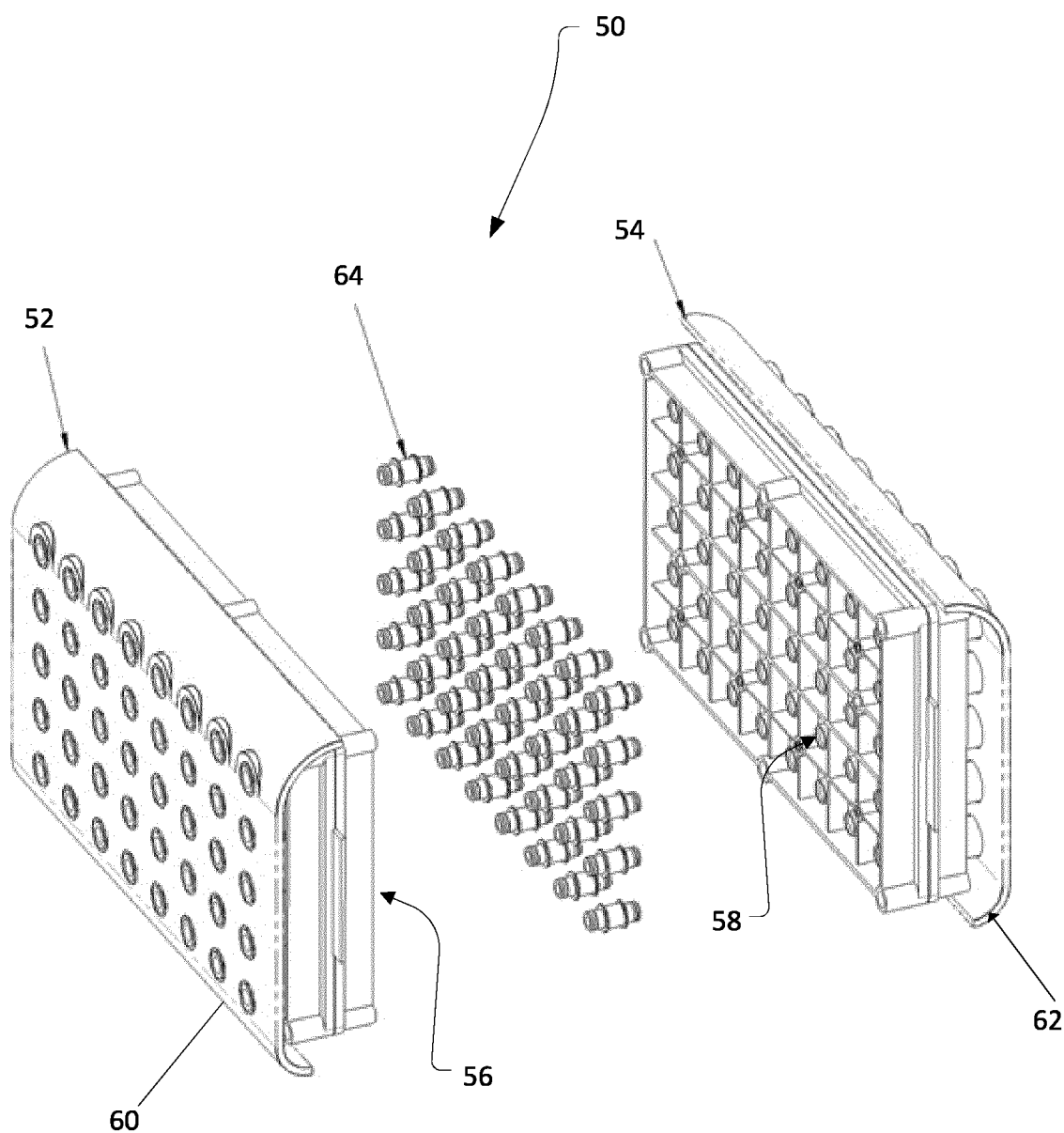
FIG. 5 is an exploded view of a multi-channel particle and/or gas detector, the detector having multiple planar arrays of detector elements, in accordance with a further example embodiment.

FIG. 5 shows a configuration of a multi-channel particle and/or gas detector 50 which comprises two arrays of detectors, each array being housed in detector sub-housings 52 and 54. Although not shown in FIG. 5, each detector sub-housing 52 and 54 comprises an array of sensors, and on each side of the array, a combination of a sealing gasket and a manifold, thereby to form a single-array sensor configuration or subassembly 56 and 58. This is similar to the arrangement shown in FIGS. 3 and 4 where the array of sensors 22 has mounted on each side a sealing gasket 32*a*, 32*b* and a manifold 34*a*, 34*b*. On the outer ends of each of the single-array sensor configurations 56 and 58 are respective pneumatic fittings 36*a*, 36*b*, an aperture fixing plate and side panels 60 and 62, which form part of the main housing of the detector 50. Similar to the descriptions above, the single-array sensor configuration 56, 58 defines multiple channels, each having an input, a sensor and an output.

The two adjacent single-array sensor configurations 56 and 58 are joined together with multiple pneumatic fittings 64, each of which has a double spigot to connect an output of a detector channel of the single-array sensor configuration 56 with an input of a detector channel of the single-array sensor configuration 58. The outlets of the detector channels of configuration 56 are therefore in fluid communication with inlets of the detector channels of configuration 58, forming a single detector channel in which two sensors are connected in series. The single detector channel is in use connected with a single sampling tube, with air from the tube flowing over both sensors of both single-array sensor configurations 56 and 58.

Although a combination of two single-array sensor configurations is shown in FIG. 5, it will be appreciated that more than two single-array sensor configurations could similarly and easily be connected together in a stacked in-line configuration, forming additional arrays of series connected detector elements to provide multiple dedicated channels.

It will further be appreciated that the structures of the manifolds forming the single-array sensor configuration could be adapted to allow adjacent manifolds to easily interlock and/or stack with each other.

It thus follows that the modular construction of the detector facilitates stacking of a plurality of sub-assemblies, the number of sub-assemblies depending on the number of in-line detectors required. Each sub-assembly may e.g., include an array of detector elements (in some instances a planar array) on opposite sides of which are mounted manifolds, preferably via sealing gaskets, the manifolds in turn being arranged to receive pneumatic fittings. The inlets or outlets of the pneumatic fittings may be configured to receive sampling tubes. For a stacking embodiment the pneumatic fittings on one or both sides of the array of detector elements (depending on how many sub-assemblies are in the stack) may have both ends configured to locate within manifolds so that a further manifold/detector array/ manifold sub-assembly may be stacked on the existing sub-assembly. The stacked sub-assemblies are in turn enclosed in a casing.

The multiple sensors connected in series within a single detector channel are typically different sensors which will allow them to detect different particles, gases, combination of particles or combination of gases. This then allows for multi-criteria detection of particles and/or gases within a particular detection channel of the detector. For example, it is expected that all sensors in one array would be the same, while the sensors will differ between the stacked arrays. The detector channels would thus be configured to detect a combination of particle or gases, in accordance with the individual sensors forming part of each detector channel.

It is also possible that two sensors in series could detect the same gas or particle, but at different concentrations, thereby allowing one detector channel with multiple sensors to provide different alarm indications for the same type of particle or gas detection.

In one example embodiment, the multi-channel particle and/or gas detector may include flow monitoring devices associated with each detector channel. For example, a flow monitoring device may be secured to an inlet or outlet of each or some channels.

The present multi-channel particle and/or gas detector also allows for a convenient and simultaneous calibration process for all detector elements (sensors) in a single array. This calibration process requires the aspirator described with reference to FIG. 2 to be switched off and/or reversed and a calibration gas to be provided at a point where the paths from each channel are common, e.g., at the plenum and then to let the calibration gas flow through the detectors.

The invention claimed is:

1. A multi-channel particle and/or gas detector including a plurality of planar arrays of detector elements held in a housing structure, each detector element having an inlet and an outlet,
    wherein the multiple planar arrays of detector elements are arranged such that outlets of one array of detector elements are in fluid communication with inlets of an adjacent array of detector elements and wherein each planar array has a manifold located on opposite sides thereof, and wherein multiple detector elements from different arrays are connected in series to form a detector channel, wherein each detector channel operatively communicates with a sampling tube.

2. The multi-channel particle and/or gas detector as claimed in claim 1 wherein at least one of said arrays of detector elements is an array of sensors of the same type thereby each detector element of an array detects the same particle, gas, combination of particles or combination of gases.

3. The multi-channel particle and/or gas detector as claimed in claim 1 wherein at least one of said arrays of detector elements includes different types of sensors, each type of sensor configured to detect a different particle, gas, combination of particles or combination of gases.

4. The multi-channel particle and/or gas detector as claimed in claim 1 wherein the multiple detector elements connected in series within a single detector channel are respectively configured to detect different particles, gases, combination of particles or combination of gases, thereby to provide multi-criteria detection of particles and/or gases within the particular detector channel of the detector.

5. The multi-channel particle and/or gas detector as claimed in claim 1 wherein the detector includes a plenum connected, on one end thereof, to a final outlet of the detector elements of the detector channels, wherein said plenum is in fluid communication with an aspirator in use causing air to flow through the arrays of detector elements.

6. The multi-channel particle and/or gas detector as claimed in claim 5 wherein the aspirator is a fan or a pump.

7. The multi-channel particle and/or gas detector as claimed in claim 1 wherein the detector includes a flow monitoring device associated with each or some of the detector channels.

8. The multi-channel particle and/or gas detector as claimed in claim 2 wherein each of the sensors includes a detecting substrate configured to detect a particular particle or gas and wherein the detecting substrate is selected from one or more of the following: a printed circuit board, a ceramic, a composite device, a semiconductor or a micro-electro-mechanical system (MEMS).

9. The multi-channel particle and/or gas detector as claimed in claim 3 wherein each of the sensors includes a detecting substrate configured to detect a particular particle or gas and wherein the detecting substrate is selected from one or more of the following: a printed circuit board, a ceramic, a composite device, a semiconductor or a micro-electro-mechanical system (MEMS).

10. The multi-channel particle and/or gas detector as claimed in claim 8 wherein the detecting substrate is communicatively coupled to the inlet and outlet of each detector element.

11. The multi-channel particle and/or gas detector as claimed in claim 1 in which either or both of a first inlet and a final outlet of each detector channel are provided by a pneumatic fitting for receiving a sampling tubes.

12. The multi-channel particle and/or gas detector as claimed in claim 9 wherein the detecting substrate is communicatively coupled to the inlet and outlet of each detector element.

13. The multi-channel particle and/or gas detector as claimed in claim 1 wherein the housing structure includes a pair of respective side panels between which is mounted the series of planar arrays of detector elements with a sealing gasket the first side thereof to create a seal between the first planar array of detector elements and an adjacent manifold, wherein the gasket isolates the sample airflow along each detector channel to a corresponding detector element.

14. The multi-channel particle and/or gas detector as claimed in claim 11 wherein the pneumatic fittings are a push-fit connection adapted to receive a flexible hose.

* * * * *